United States Patent [19]

Stefanchik

[11] 4,220,451
[45] Sep. 2, 1980

[54] PROCESS FOR THE DETERMINATION OF SERUM INORGANIC PHOSPHATE

[75] Inventor: John A. Stefanchik, Bronx, N.Y.

[73] Assignee: Union Carbide Corporation, New York, N.Y.

[21] Appl. No.: 5,875

[22] Filed: Jan. 23, 1979

[51] Int. Cl.² ...................... G01N 33/16; G01N 21/22
[52] U.S. Cl. ................................... 23/230 B; 23/916; 252/408
[58] Field of Search ............... 23/230 B, 916; 252/408

[56] References Cited

U.S. PATENT DOCUMENTS

| 3,795,484 | 3/1974 | Daly | 23/230 B |
| 3,853,469 | 12/1974 | Morin | 23/230 B |
| 3,874,853 | 4/1975 | Byrnes | 23/230 B |

OTHER PUBLICATIONS

Clinical Chemistry, 15, p. 807 (1969).

Primary Examiner—Sidney Marantz
Attorney, Agent, or Firm—William Raymond Moran

[57] ABSTRACT

A process for the determination of serum inorganic phosphate utilizing a centrifugal analytical photometer. By optimizing the concentration of surfactant and surfactant media, the reaction rate is increased and the pretest mixing time reduced. The improved process is particularly useful for the rapid and accurate determination of inorganic phosphate in body fluids, such as blood serum.

5 Claims, No Drawings

PROCESS FOR THE DETERMINATION OF SERUM INORGANIC PHOSPHATE

This invention relates in general to an improved process for the determination of serum inorganic phosphate in fluids, particularly body fluids. In one aspect, the invention relates to an improved process for the determination of inorganic phosphate in blood serum. In a further aspect the invention relates to an improved process for the determination of phosphate using a centrifugal analytical photometer.

In recent years the need for more sophisticated quantitive analytical methods has increased markedly due to the numerous microanalytical studies in biochemical research, routine clinical testing for physicians and hospitals, and the like. In addition to the increased demand for new methods of analysis, in certain field it is often highly desirable that the method be simple to perform, be rapid and yet provide consistently reliable results. This is particularly important for clinical testing of body fluids where a proper diagnosis of treatment often depends upon the information provided by analyses. However, few methods are available which can rapidly and accurately handle the increasing number and varied test desired by clinicians.

For example, the determination of inorganic phosphate in body fluids, such as blood serum, is assuming a steadily growing share of the clinical laboratory's work load. The determination of phosphate in serum is important in several diseases in particular uremia and chronic renal diseases where phosphate retention occurs. Only the so-called inorganic phosphate is estimated since the significance of changes in phospholipids, phosphate esters and nucleotide phosphate is not easily related to clinical problems. However, in spite of the advent of many new chemical methods, the photometric determination of inorganic phosphate in biological samples is conventionally performed by the use of the molybdenum blue reaction (I. M. Kolthoff and P. D. Elving, Eds., Part II, Vol. 5, pages 317–402, 1961).

U.S. Pat. No. 3,795,484, which issued on Mar. 5, 1974, and is assigned to the same assignee as the invention, discloses a process for the determination of inorganic phosphate by a method which utilizes a centrifugal automatic analyzer. Analytical photometers which utilize a centrifugal field have recently become available for the rapid microanalysis of a wide variety of liquids such as body fluids, e.g., blood serum, food products, and the like. Since numerous analyses can be performed rapidly and simultaneously these devices are of particular interest wherein a large number of samples is involved or a variety of tests on one sample is desired. Moreover, since these devices allow the use of relatively small volumes of reagents, i.e., in the microliter range, the use of expensive reagents can be minimized.

One such device which utilizes a centrifugal field in microanalytical studies is an instrument marketed by Union Carbide Corporation under the trademark, "CentrifiChem". This device employs the principle of double-beam spectrophotometry wherein absorbances of a liquid sample and a reference solution are intercompared. The system as originally disclosed in U.S. Pat. No. 3,555,284 is basically a series of cuvets arranged around the periphery of a rotor so that when it is spun, centrifugal force transfers reagents and samples to the cuvets where the concentration is measured spectrophotometrically. A sample loading disk is provided which consists of rows of cavities arranged concentrically. Reagents are placed in the inner-most cavity and serum samples in the center cavity of the sample loading disk which is then indexed and positioned in the rotor with each reagent and serum sample having its respective cuvet. As the rotor is accelerated, centrifugal force moves the reagents and sample to the outer-most cavity where they are transferred through small channel to the cuvet. During the transfer, the reagent and sample mix. The filled cuvets rapidly spin past the fixed light beam and the transmission of light is measured.

As indicated in U.S. Pat. No. 3,795,484, most of the earlier approaches for the determination of inorganic phosphate involve the use of the molybdenum blue reaction. This reaction involves the formation of a phosphate molybdate complex which is subsequently reduced by means of stannous chloride, phenylhydrazine, ascorbic acid, amino naphtholsulfonic acid or other reducing agents. A blue colored complex of the reduced heteropolyacid is formed and the absorbance of the complex measured at around 700 nm (nanometers). The preparation of a protein free serum sample is required for this test, which makes the test cumbersome to perform. Additionally, the sensitivity of the test is low. Moreover, in order to perform the test properly, at least two sequential additions of reagents are required.

Attempts to measure inorganic phosphate by means of the yellow molybdovanadophosphate heteropolyacid have been suggested but have failed to date to become accepted as a routine procedure. Even less effort has been made to quantitate the unreduced phosphomolybdate complex prior to its reduction. The absorbance maximum of this heteropolyacid complex lies in the ultraviolet range and high sample and reagent blanks have to be eliminated.

The process disclosed in U.S. Pat. No. 3,795,484, involved mixing a phosphate containing fluid and an ammonium molybdate solution and measuring changes in absorbance due to their interaction over a predetermined period of time, as indicated in the patent. In view of the fact that a linear relationship exists between the change of absorbance and the phosphate concentration, up to at least 10 milligram per 100 milliliters of phosphate can be measured.

However, in the patented process disclosed, it is indicated that the initial absorbance reading is taken at 2.0 seconds and a final reading at 10 minutes. Although not mentioned in the procedure, the pretest mixing time is usually of the order of 30 minutes. In contrast, it has now been found that by optimizing the concentration of surfactant and surfactant media, the reaction rate can be reduced from 10 minutes to from 2 to 4 minutes and the pretest mixing time from 30 to 5 minutes, or less.

It is, therefore, an object of this invention to provide an improved process for the determination of inorganic phosphate. Another object of the invention is to provide a process for the determination of inorganic phosphate in body fluids wherein the pretest mixing time of reagents is reduced. A further object of the invention is to provide an improved process wherein the reaction rate of ammonium molybdate and inorganic phosphate is accelerated. A still further object of this invention is to provide a process for the determination of inorganic phosphate in blood serum which can be accomplished in a shorter time than by previously known methods. These and other objects will readily become apparent to those skilled in the art in the light of the teachings herein set forth.

In its broad aspect, this invention relates to an improved process for the determination of serum inorganic phosphate utilizing a centrifugal analytical photometer. The improvement comprises utilizing the surfactant as a solution in a lower alkanol, such as methanol, wherein the ratio of surfactant to alkanol is within the range of from about 20:80 to about 80:20 by volume.

By optimizing the surfactant concentration and employing a lower alkanol as the surfactant medium, it has been observed that the premix time can be considerably shortened and the overall reaction rate increased. Accordingly, the improved process of this invention permits the analysis for serum inorganic phosphate to be carried out in a shorter period of time without any sacrifice in accuracy. By using a preferred 50:50 mixture by volume of methanol and surface active agent, marked improvement in the time required to conduct the analysis is readily achieved. In view of the numerous analyses being conducted daily in hospitals and commercial laboratories, savings of as little as a few minutes per analysis can greatly effect the overall economics of such operations.

Although a wide variety of surface active agents can be employed, it has been found that the non-ionic surface active agents are preferred. Illustrative agents include among others, the sorbitan monooleates, sold by Fischer Scientific under the trademark "Tween". "Tween-80" is particularly effective in eliminating protein interference. The amount of surface active agent employed need only be such as will prevent precipitation and turbidity. In U.S. Pat. No. 3,795,484 it was disclosed that if the molybdate solution contains from about 0.1 to about 1.0 percent of the surface active agent mixed with water, protein interference is suppressed. However, in the process of the present invention, it was found that if the surface active agent is employed as a 50:50 mixture by volume with methanol, rather than water, that the pretest mixing time is reduced from about 30 minutes to about 5 minutes or less, and the reaction rate increased such that the concentration can be measured in four minutes or less.

The following example illustrates the best mode presently contemplated for practicing the process of this invention:

EXAMPLE 1

This experiment was conducted to determine the effects of different concentrations of surfactant contained in methanol on the rate of reaction and its linearity. Samples were prepared containing 10, 40, 60 and 90 milliliters of Tween 80 in 90, 60, 40 and 10 milliliters of methanol respectively. After mixing, 0.45 milliliters of the surfactant solution were added to 13.0 milliliters of an ammonium molybdate solution which contained 2 grams of $(NH_4)_6MO_7O_{24} \cdot 4H_2O$ in one liter of 1.2 N $H_2SO_4$. The mixture was ready for use within 5 minutes after mixing. Standard phosphorus samples were prepared containing 2, 4, 5, 7, 10, 12, 14, 16, 18 and 20 milligram per hundred milliliters of solution. Using a CentrifiChem Automatic Analyzer, and measuring the absorbance at 2 minute and 4 minute intervals, the observed and theoretical phosphorus concentrations were compared: the results in table I below set forth the percent completion of the reaction for the 18 milligram standard and the linearity.

Table I

| Volume | Percent Completed | | Linearity | |
|--------|:----:|:----:|:----:|:----:|
| Tween 80 | 2 Min. | 4 Min. | 2 Min. | 4 Min. |
| 10ml | 91 | 98 | 12 mg% | 20 mg% |
| 40ml | 95 | 98 | 20 mg% | 20 mg% |
| 60ml | 100 | 100 | 20 mg% | 20 mg% |
| 90ml | 98 | 99 | 20 mg% | 20 mg% |

Although the invention has been illustrated by the preceding disclosure, it is not to be construed as being limited to the particular embodiments or materials disclosed therein. Rather, the invention encompasses the generic area hereinbefore disclosed. Various modifications and embodiments thereof can be made without departing from the spirit and scope thereof.

What is claimed is:

1. In a process for the determination of serum inorganic phosphate in a phosphate-containing body fluid wherein such determination is made utilizing a centrifugal analytical photometer and wherein a mixure is formed of said phosphate-containing body fluid and an ammonium molybdate solution in the presence of a surface active agent, the improvement which comprises utilizing said surfactant as a solution in a lower alkanol wherein the ratio of surfactant to alkanol is within the range of from about 20:80 to about 80:20 by volume.

2. The process of claim 1 wherein said alkanol is methanol.

3. The process of claim 1 wherein said surfactant is a non-ionic surface-active agent.

4. The process of claim 1 wherein said surfactant is a sorbitan monooleate.

5. The process of claim 1 wherein said ratio of surfactant to alkanol is 50:50 by volume.

* * * * *